US011846184B2

(12) United States Patent
Wang et al.

(10) Patent No.: US 11,846,184 B2
(45) Date of Patent: Dec. 19, 2023

(54) SYSTEMS AND METHODS FOR PREDICTING THE COMPOSITION OF PETROLEUM HYDROCARBONS

(71) Applicant: ExxonMobil Technology and Engineering Company, Spring, TX (US)

(72) Inventors: David T. Wang, Witchita Falls, TX (US); Cara L. Davis, Houston, TX (US); Michael J. Formolo, The Woodlands, TX (US); Sarah E. Gelman, Lakewood, CO (US); Michael Lawson, Spring, TX (US); Clifford C. Walters, Milford, NJ (US); Yitian Xiao, Sugar Land, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 167 days.

(21) Appl. No.: 17/305,061

(22) Filed: Jun. 30, 2021

(65) Prior Publication Data
US 2022/0042413 A1     Feb. 10, 2022

Related U.S. Application Data

(60) Provisional application No. 62/706,210, filed on Aug. 5, 2020.

(51) Int. Cl.
*E21B 49/08*     (2006.01)
*G01N 33/28*     (2006.01)
(Continued)

(52) U.S. Cl.
CPC ............ *E21B 49/087* (2013.01); *G01N 33/24* (2013.01); *G01N 33/2823* (2013.01);
(Continued)

(58) Field of Classification Search
CPC ............... E21B 49/087; E21B 49/0875; E21B 2200/20; E21B 33/00; G01V 99/005
See application file for complete search history.

(56) References Cited

U.S. PATENT DOCUMENTS

| 7,344,889 B2 | 3/2008 | Kelemen et al. |
| 7,979,216 B2 | 7/2011 | Fusetti et al. |
| | (Continued) | |

FOREIGN PATENT DOCUMENTS

| FR | 2906481 A1 | 4/2008 |
| FR | 2906482 A1 | 4/2008 |

OTHER PUBLICATIONS

Chen, Z., et al. (2002) "Integrated two-dimensional modeling of fluid flow and compaction in a sedimentary basin", Computational Geosciences, vol. 6, pp. 545-564.
(Continued)

*Primary Examiner* — Catherine Loikith
(74) *Attorney, Agent, or Firm* — Lempia Summerfield Katz LLC (57) ABSTRACT

A quantitative simulation process for producing quantitative model predictions of hydrocarbon composition. The quantitative simulation may include measuring a chemical and isotopic composition of a hydrocarbon sample from a hydrocarbon reservoir. The quantitative simulation may further include measuring geochemical data, geophysical data, and/or geological data for the hydrocarbon reservoir and/or source rock; deriving temperature versus time relationships from a basin model for the hydrocarbon reservoir and/or source rock based on the geochemical data, geophysical data, and/or geological data; generating estimated source-rock maturity parameters based on the temperature versus time relationships; generating an estimated compositional yield for hydrocarbon fractions based on the temperature versus time relationships and the chemical composition of
(Continued)

the hydrocarbon sample; and generating, using a mass-conserving isotopic fraction (MCIF) simulator, an estimated isotopic composition of the hydrocarbon fractions based on the estimated compositional yield and the isotopic composition of the hydrocarbon sample.

15 Claims, 6 Drawing Sheets

(51) Int. Cl.
  *G06F 30/20* (2020.01)
  *G01V 99/00* (2009.01)
  *G01N 33/24* (2006.01)
(52) U.S. Cl.
  CPC ............ *G01V 99/005* (2013.01); *G06F 30/20* (2020.01); *E21B 2200/20* (2020.05)

(56) References Cited

U.S. PATENT DOCUMENTS

| | | | | |
|---|---|---|---|---|
| 8,165,817 | B2* | 4/2012 | Betancourt | G01V 11/00 |
| | | | | 73/152.09 |
| 8,352,228 | B2 | 1/2013 | Walters et al. | |
| 9,552,462 | B2 | 1/2017 | Walters et al. | |
| 9,890,617 | B2* | 2/2018 | Lawson | G01V 9/007 |
| 10,083,258 | B2* | 9/2018 | Kauerauf | G06F 30/20 |
| 2010/0161302 | A1 | 6/2010 | Walters et al. | |
| 2010/0223039 | A1 | 9/2010 | Maliassov | |
| 2016/0098543 | A1 | 4/2016 | Salmon et al. | |

OTHER PUBLICATIONS

Davis, J.S., et al. (2012) "Modeling Gas Migration, Distribution, And Saturation In A Structurally And Petrologically Evolving Tight Gas Reservoir", International Petroleum Technology Conference, Bangkok, Thailand, IPTC 14621, pp. 1-12.
Walters, C.C., et al. (2007) "Predicting oil and gas compositional yields via chemical structure-chemical yield modeling (CS-CYM): Part 2—Application under laboratory and geologic conditions", Organic Geochemistry, vol. 38, pp. 306-322.
Freund, H., et al. (2007) "Predicting oil and gas compositional yields via chemical structure-chemical yield modeling (CS-CYM): Part 1—Concepts and implementation", Organic Geochemistry, vol. 38, pp. 288-305.
Fjellanger, E., et al. (2010) "Charging the giant gas fields of the NW Siberia basin" in Petroleum Geology: From Mature Basins to New Frontiers—Proceedings of the 7th Petroleum Geology Conference edited by Vining, B.A., et al., pp. 659-668.
Lewis C.A. (1993) "The Kinetics of Biomarker Reactions" in Organic Geochemistry, Topics in Geobiology edited by Engel M.H. et al., vol. 11, Springer, Boston, MA, pp. 491-510.
Burnham A.K., et al. (1989) "A chemical kinetic model of vitrinite maturation and reflectance", Geochmica et Cosmochemica Acta, vol. 53, Issue 10, pp. 2649-2657.
Chung H.M., et al. (1979) "Use of stable carbon isotope compositions of pyrolytically derived methane as maturity indices for carbonaceous materials", Geochmica et Cosmochemica Acta, vol. 43, Issue 12, pp. 1979-1988.
Hantschel T., et al. (2009) "Petroleum Generation", Fundamentals of Basin and Petroleum Systems Modeling, pp. 151-198.
Pepper A.S., et al. (1995) "Simple kinetic models of petroleum formation. Part I: oil and gas generation from kerogen", Marine and Petroleum Geology, vol. 12, No. 3, pp. 291-319.
Pepper A.S., et al. (1995) "Simple kinetic models of petroleum formation. Part II: oil-gas cracking", Marine and Petroleum Geology, vol. 12, No. 3, pp. 321-340.
Pepper A.S., et al. (1995) "Simple kinetic models of petroleum formation. Part III: Modelling an open system", Marine and Petroleum Geology, vol. 12, No. 4, pp. 417-452.
Chung H.M., et al. (1988) "Origin of Gaseous Hydrocarbons in Subsurface Environments: Theoretical Considerations of Carbon Isotope Distribution", Chemical Geology, vol. 71, pp. 97-103.
Rooney M.A., et al. (1995) "Modeling thermogenic gas generation using carbon isotope ratios of natural gas hydrocarbons", Chemical Geology, vol. 126, pp. 219-232.
Tang Y., et al. (2000) "Mathematical modeling of stable carbon isotope ratios in natural gases", Geochimica et Cosmochimica Acta, vol. 64, No. 15, pp. 2673-2687.
Wang DT (2017) "The Geochemistry of Methane Isotopologues", Thesis at Massachusetts Institute of Technology and Woods Hole Oceanographic Institution, doi:10.1575/1912/9052, pp. 1-92.
Xiao Y. (1997) "Understanding the Kinetics and Mechanisms of Hydrocarbon Thermal Cracking: An Ab Initio Approach", Ind. Eng. Chem. Res., vol. 36, pp. 4033-4044.
Tissot BP, et al. (1987) "Thermal History of Sedimentary Basins, Maturation Indices, and Kinetics of Oil and Gas Generation", AAPG Bulletin, vol. 71, No. 12, pp. 1445-1466.
Hood A., et al. (1975) "Organic Metamorphism and the Generation of Petroleum", AAPG Bulletin, vol. 59, No. 6, pp. 986-996.
Sweeney J.J., et al. (1990) "Evaluation of a Simple Model of Vitrinite Reflectance Based on Chemical Kinetics", AAPG Bulletin, vol. 74, No. 10, pp. 1559-1570.
Magoon LB, et al. (1994) "The Petroleum System", Chapter 1 in The Petroleum System—From Source to Trap, AAPG Memoir, vol. 60, pp. 3-24.
Whiticar M.J. (1994) "Correlation of Natural Gases with Their Sources" Chapter 16 in The Petroleum System—From Source to Trap, AAPG Memoir, vol. 60, pp. 261-283.
Wang DT (2017) "The Geochemistry of Methane Isotopologues", Thesis at Massachusetts Institute of Technology and Woods Hole Oceanographic Institution, doi:10.1575/1912/9052, pp. 93-144.
Xiao, Y. (2001) "Modeling the kinetics and mechanisms of petroleum and natural gas generation: a first principles approach", Reviews in Mineralogy and Geochemistry 42, pp. 383-436.

* cited by examiner

SYSTEMS AND METHODS FOR PREDICTING THE COMPOSITION OF PETROLEUM HYDROCARBONS

CROSS-REFERENCE TO RELATED APPLICATIONS

This application claims the benefit of U.S. Provisional Application No. 62/706,210, filed Aug. 5, 2020, the entirety of which is incorporated by reference herein.

FIELD OF INVENTION

The present disclosure relates to systems and methods for predicting the chemical and isotopic composition of petroleum hydrocarbons.

BACKGROUND

Basin modeling is the process of using either proprietary or commercially available software to assess charge risk by integrating diverse geological and engineering data types into a model of one or more petroleum systems active in an area being explored. The scale of the model may range in size from a single drilling prospect to an entire basin.

Generally, the composition of hydrocarbons sampled during hydrocarbon exploration or production reflect the integrated history of source rock maturation and hydrocarbon generation, accumulation, and alteration. The composition of hydrocarbons are conventionally used to provide qualitative assessments of maturity, gas origin, or biological alteration using simple empirical schemes within the basin model.

There are several commercial basin simulators (or basin modeling packages) that are widely used in academia and industry. Such packages contain prediction algorithms or modules which base the kinetics of petroleum generation on some form of a series of parallel first-order reactions, each individual reaction describing the breakdown of one fraction of a kerogen, oil, or gas molecular "lump" (or component). The reaction rate of each parallel reaction is usually as a temperature-dependent function that follows the Arrhenius Equation. In parallel-Arrhenius kinetic models, each reaction has as a discrete spectrum of activation energies ($E_a$). These kinetic models comprise a distribution of $E_a$'s at fixed or variable spacing (typically 1 kcal/mole) using a single or varying frequency factor (A). The parameters for these kinetic models are based on various laboratory experiments. Some known kinetic models rely on simple compositional models that are rooted in a petroleum modeling computer program called PMOD developed and made available by the Lawrence Livermore National Laboratory. Additionally, some models predict compositional yields models based on forms of pyrolysis, including open-system pyrolysis. Other models use a compositional yields model based on open and closed-system pyrolysis. Models that predict compositional yields as defined by varying chemical lumps are expressed typically by the bulk kerogen yield kinetic model (discrete $E_a$'s; fixed or varying A) where the percentage of each chemical lump is defined for each individual $E_a$.

Further development and refinement of such models that quantitatively predict the volumes and compositions of hydrocarbons from the properties of a presumed source rock are needed that provide further information that potentially constrain key risks encountered in petroleum exploration, particularly the petroleum system elements of charge timing, relative hydrocarbon yield versus time, and source type.

SUMMARY OF INVENTION

The present disclosure relates to systems and methods for predicting the chemical and isotopic composition of petroleum hydrocarbons. More specifically, the systems and methods of the present disclosure relate to a Mass-Conserving Isotopic Fraction simulator (MCIF simulator) that is embedded within a quantitative simulation process incorporating a basin model and data to produce quantitative model predictions of hydrocarbon composition.

The present disclosure includes is quantitative simulation process comprising: measuring a chemical and isotopic composition of a hydrocarbon sample from a hydrocarbon reservoir; measuring geochemical data, geophysical data, and/or geological data for the hydrocarbon reservoir and/or source rock; deriving temperature versus time relationships from a basin model for the hydrocarbon reservoir and/or source rock based on the geochemical data, geophysical data, and/or geological data; generating estimated source-rock maturity parameters based on the temperature versus time relationships; generating an estimated compositional yield for hydrocarbon fractions from the hydrocarbon reservoir based on the temperature versus time relationships and the chemical composition of the hydrocarbon sample; generating, using a MCIF simulator that uses ab initio calculations, an estimated isotopic composition of the hydrocarbon fractions based on the estimated compositional yield and the isotopic composition of the hydrocarbon sample; and performing a hydrocarbon management operation in the hydrocarbon reservoir based on the estimated source-rock maturity parameters, the estimated compositional yield, and the estimated isotopic composition.

The present disclosure includes a computing system comprising: a processor; a non-transitory, computer-readable medium comprising a quantitative simulation process that derives an estimated source-rock maturity parameters, an estimated compositional yield, and an estimated isotopic composition for a hydrocarbon reservoir; a non-transitory, computer-readable medium comprising instructions configured to: accept inputs that include geochemical data, geophysical data, and/or geological data for the hydrocarbon reservoir and a chemical and isotopic composition of a hydrocarbon sample from the hydrocarbon reservoir; and run the quantitative simulation process that comprises: a basin model for the hydrocarbon reservoir that produces temperature versus time relationships based on the geochemical data, geophysical data, and/or geological data; a maturity kinetic simulator that produces estimated source-rock maturity parameters based on the temperature versus time relationships; a compositional simulator that produces an estimated compositional yield for hydrocarbon fractions from the hydrocarbon reservoir based on the temperature versus time relationships and the chemical composition of the hydrocarbon sample; a mass-conserving isotopic fraction simulator, which uses ab initio calculations, that produces an estimated isotopic composition of the hydrocarbon fractions based on the estimated compositional yield and the isotopic composition of the hydrocarbon sample; and output the estimated source-rock maturity parameters, the estimated compositional yield, and the estimated isotopic composition.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION

The present disclosure relates to systems and methods for predicting the chemical and isotopic composition of hydrocarbons. More specifically, the systems and methods of the present disclosure relate to the MCIF simulator that is incorporated with a basin simulation to produce quantitative predictions via a quantitative simulation process. The MCIF simulator described herein has the ability to simulate the chemical and isotopic composition of hydrocarbons that accumulate using varying assumptions about trap timing. Advantageously, this provides a more detailed understanding of the hydrocarbon system including informing the relative hydrocarbon yield versus time. The relative hydrocarbon yield versus time estimates can be used in deciding when or whether to produce a known or prospective hydrocarbon reservoir.

As used herein, the term "hydrocarbon reservoir" refers to a subsurface body of rock(s) containing hydrocarbons. The body of rock(s) may range in size from a single layer of rock of interest for a single drilling site to a basin with many layers and types of rocks.

As used herein, the term "hydrocarbon system" comprises all the geologic units and factors that relate to the formation of a hydrocarbon reservoir. Geologic units include a source rock, reservoir rock, seal rock, and overburden, and factors include the formation of a hydrocarbon trap and the burial of source rock to adequate depth and temperature (Magoon, L. B., Dow, W. G., 1994. The petroleum system: Chapter 1: Part I. Introduction, in: Magoon, L. B., Dow, W. G. (Eds.), The Petroleum System—from Source to Trap, AAPG Memoir. pp. 3-24).

The systems and methods of the present disclosure include a quantitative simulation process that relates the chemical and isotopic composition of a hydrocarbon sample from a hydrocarbon reservoir to the development of an associated hydrocarbon system and comprises three components: (i) time-temperature history; (ii) compositional yield solver; and (iii) the MCIF simulator.

Figure 1:
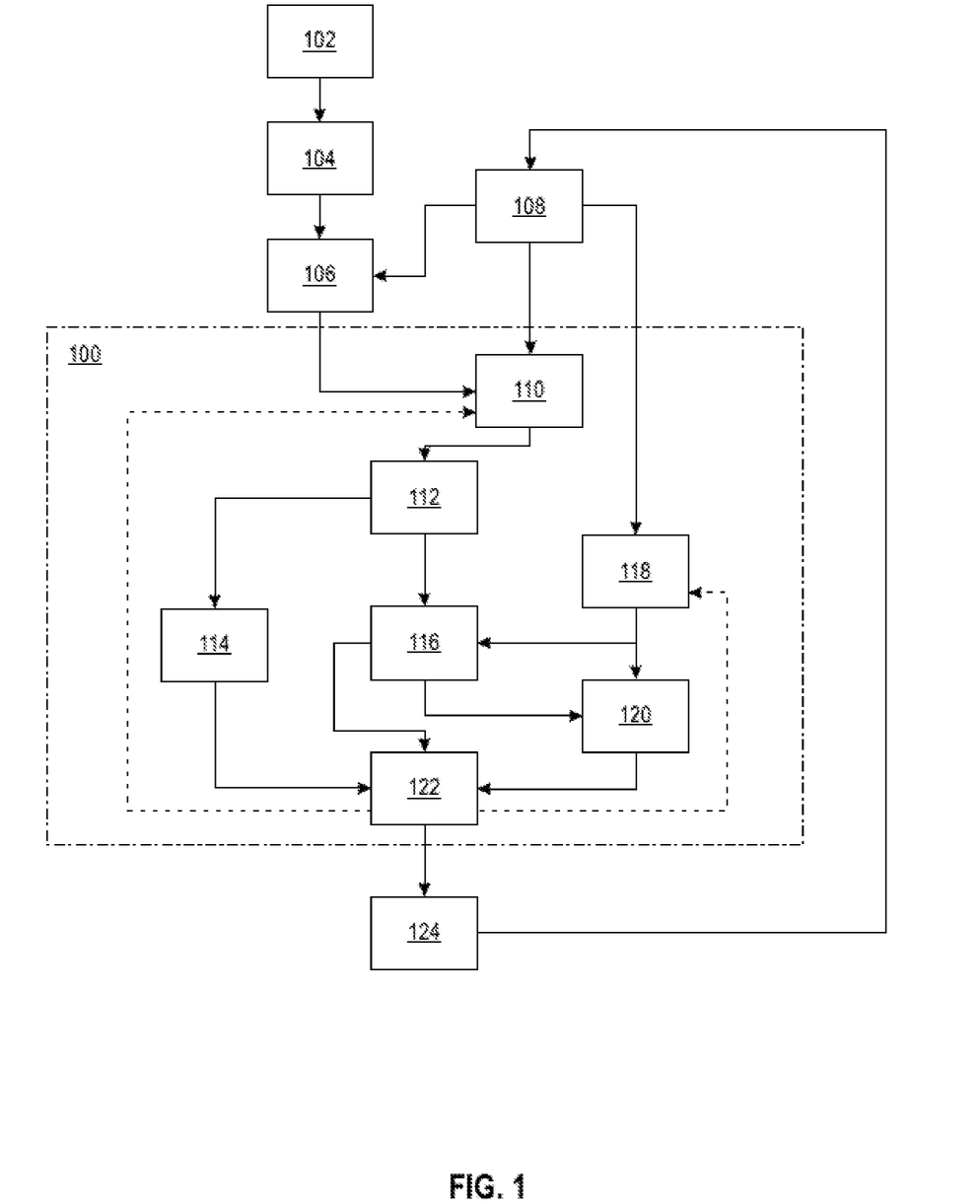
FIG. 1 illustrates a nonlimiting example of a quantitative simulation process of the present disclosure, its inputs, and its outputs.

FIG. 1 illustrates a nonlimiting example of a quantitative simulation process 100 of the present disclosure. The quantitative simulation process 100 includes the construction and interpretation of a basin model 110, which is a visualization of the hydrocarbon reservoir of interest. The basin model 110 may be a 1-dimensional, 2-dimensional, or 3-dimensional time-dependent model of the hydrocarbon reservoir. The basin model 110 is developed based on data inputs 106 (more specifically, a kinetic model 106) and 108.

Input 106 is a kinetic model derived from data 102 that describes or relates to the maturation of hydrocarbons from sedimentary organic material. The data 102 can include measured data, simulated data, or a combination thereof. For example, the data 102 can be measured on source rocks, presumed source rocks, synthetic core samples, or other suitable rock or core samples containing petroleum hydrocarbons. Said hydrocarbons in said samples are then artificially matured under defined temperature and pressure conditions. In another example, a basin model may be constructed to simulate the maturation of hydrocarbons in a hydrocarbon reservoir at various temperature and pressure conditions. Nonlimiting examples of such basin models are described in US Pat. App. Pub. No. 2010/0223039; Z. Chen, et al. (2002) "Integrated Two-Dimensional Modeling of Fluid Flow and Compaction in a Sedimentary Basin", Computational Geosciences, Vol. 6, pp. 545-564; J. S. Davis, et al. (2012) "Modeling Gas Migration, Distribution, And Saturation In A Structurally And Petrologically Evolving Tight Gas Reservoir", Presented at the IPTC 2012: International Petroleum Technology Conference, Bangkok, Thailand; and E. Fjellanger, et al., Charging the giant gas fields of the NW Siberia basin, in: Vining, B. A., Pickering, S. C. (Eds.), Petroleum Geology: From Mature Basins to New Frontiers Proceedings of the 7th Petroleum Geology Conference. Geological Society of London, pp. 659-668; each of which is incorporated herein by reference.

The data 102 (measured, simulated, or both) is used to derive estimates of kinetic parameters 104 that describe how fractions of hydrocarbons (e.g., gas, oil, and solid organic matter) are generated and/or consumed during thermal maturation. The estimated kinetic parameters 104 are then used to derive a kinetic model 106 that describes the rates of individual reactions within a reaction network characterizing the various fractions of hydrocarbons. The kinetic model 106 may accept or require as inputs information from data 108, for example, the organic richness (total organic carbon or TOC content) and hydrogen index (HI) for the source rocks (or presumed source rocks).

Input 108 includes geochemical data, geophysical data, and/or geological data, each of which may be derived via direct and/or measurements. Such inputs may be from or derived from, for example, seismic surveys, seepage surveys, well logs, sediment or rock core analyses, outcrop studies, remote sensing data, electromagnetic soundings, gravity surveys, chemical analyses of hydrocarbon samples, isotopic analyses of hydrocarbon samples, and the like, and any combination thereof.

Examples of basin modeling packages used to create basin model 110 include, but are not limited to, STELLAR™ (ExxonMobil), CAULDRON™ (Shell), GENESIS™ (ARCO), PERMEDIA™ (Halliburton), PBM-PARS™ BASIN MODELER (Research Institute of Petroleum Industry), PETROMOD™ (Schlumberger), BASINMOD™ (Platte River Associates, Inc.), GENEX, TEMIS™ 2D,3D (Beicip/IFP), MIGRI™, MIGRIX™ (Migris), SIGMA2D™ (JNOC/TRC), NOVVA™ (Sirius Exploration Geochemistry Inc.), and GENESIS-TRINITY™ (Zetaware).

Figure 2A:
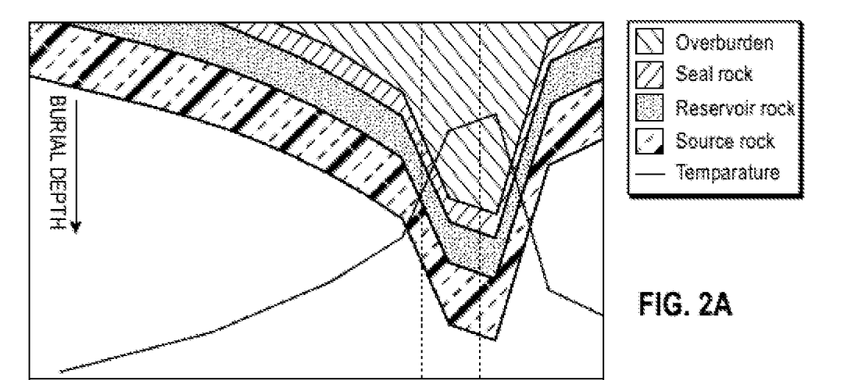
FIG. 2A depicts a time-temperature history curve for a source rock, calculated from the underlying burial history plot for a generic sequence of rock formations consisting of a source rock, a reservoir rock, a seal rock, and overburden.

The quantitative simulation process 100 extracts a time-temperature history 112 from the basin model 110. FIG. 2A is a nonlimiting, theoretical example of a time-temperature history plot.

The time-temperature history is then processed as an input for a compositional yields simulator 116. The compositional yields simulator 116 applies a multi-component parallel first-order cracking scheme in which different fractions (J) of hydrocarbons (e.g., $C_1$, $C_2$, $C_{15+}$, asphaltenes, NSO, coke) are first generated from a pre-defined kerogen precursor, and then undergo a set of cascading cracking reactions. As used herein, "NSO" or "NSOs" refers to nitrogen, sulfur, and oxygen containing compounds (also known as polars). "Coke" and "char" refer to, respectively, labile (reactive) and inert (nonreactive) classes of amorphous solid organic material (sometimes known as pyrobitumen) formed as a byproduct of petroleum-generating or cracking reactions. Coke may react to form char but char does not react to form any other component. Hence, char is the terminal, hydrogen-depleted product of catagenesis.

Figure 2B:
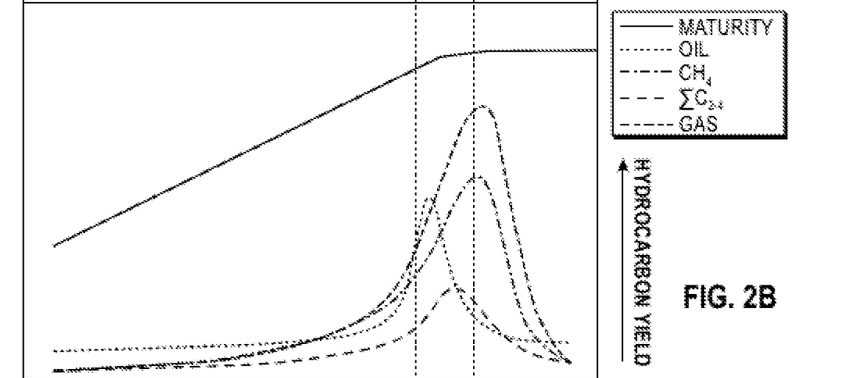
FIG. 2B illustrates a yield vs. time plot for various hydrocarbon fractions along with a representation of thermal maturity level.

The compositional yields simulator 116 models the amount and composition of generated and expelled hydrocarbons using a framework cascading cracking scheme that defines the possible reactions where hydrocarbons are assigned as individual hydrocarbons and/or lumped hydrocarbons (or hydrocarbon fraction (J)). The compositional yields simulator 116 allocates a calibrated percentage of each hydrocarbon fraction (J) into $n_{bias}$ discrete activation energy ($E_a$) bins (I) that are then cracked via Arrhenius rate laws. The result of this compositional generation kinetic calculation is a yield versus time plot for each hydrocarbon fraction or combinations of hydrocarbon fractions (FIG. 2B).

Figure 3:
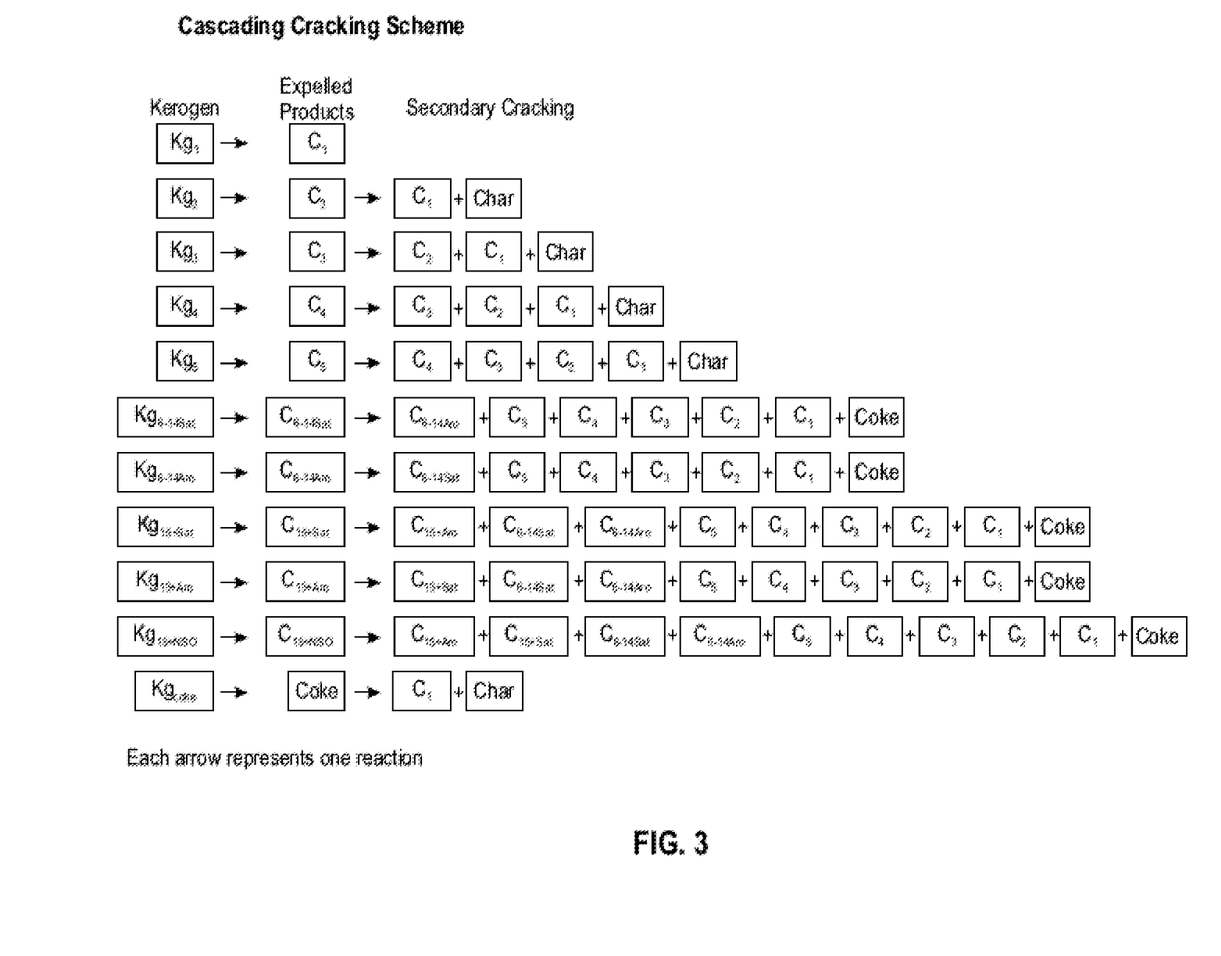
FIG. 3 illustrates a 23-component cascading cracking scheme with individual hydrocarbons defined as $C_1$, $C_2$, $C_3$, $C_4$, and $C_5$ and lumped hydrocarbon classes defined as $C_6$-$C_{14}$ aromatics, $C_6$-$C_{14}$ saturates, $C_{15+}$ saturates, $C_{15+}$ aromatics, $C_{15+}$ NSOs, coke, and char.

FIG. 3, for example, is a 23-component cascading cracking scheme with individual hydrocarbons defined as $C_1$, $C_2$, $C_3$, $C_4$, and $C_5$ and lumped hydrocarbons defined as $C_6$-$C_{14}$ aromatics, $C_6$-$C_{15}$ saturates, $C_{15+}$ saturates, $C_{15+}$ aromatics, $C_{15+}$ NSOs, coke, and char. Other cascading cracking schemes and/or other definitions for the individual and/or lumped hydrocarbons can be used.

A nonlimiting example of a particular implementation of a compositional yields simulator 116, generally known as a chemical structure-chemical yield model (CS-CYM), is described in U.S. Pat. Nos. 7,344,889, 8,352,228, and 9,552,462 and U.S. Patent Application Publication No. 2010/0161302, which are incorporated herein by reference. A CS-CYM is also described in the following publication: Freund H., Walters, et al. (2007) "Predicting Oil and Gas Compositional Yields via Chemical Structure-Chemical Yield Modeling (CS-CYM): Part 1—Concepts and Implementation", Organic Geochemistry, Vol. 38, pp. 288-305, which is incorporated herein by reference.

The quantitative simulation process 100 also includes a maturity kinetic simulator 114 that calculates the expected values of source-rock maturity parameters based on the time-temperature history 112. Examples of maturity parameters include, but are not limited to, vitrinite reflectance, level of organic metamorphism (LOM), and biomarker isomerization/aromatization parameters (e.g., Tissot, B., et al. (1987) "Thermal history of sedimentary basins, maturation indices, and kinetics of oil and gas generation", AAPG Bulletin 71, pp. 1445-1466; Hood, A., et al. (1975) "Organic metamorphism and the generation of petroleum", AAPG Bulletin 59, pp. 986-996; Lewis C. A. (1993) "The Kinetics of Biomarker Reactions: Implications for the Assessment of the Thermal Maturity of Organic Matter in Sedimentary Basins", Chapter 22 in Organic Geochemistry edited by Engel M. H., et al. (eds.), Vol. 11, pp. 491-510). Maturity parameters may be measured and/or simulated by a maturity kinetic simulator. A nonlimiting example of a particular implementation of a maturity kinetic simulator is EASY % Ro, a model based on parallel-Arrhenius first-order rate laws which calculates vitrinite reflectance as a function of time and temperature. The EASY % Ro model and its theoretical basis is described in the following references: Burnham, A. K., et a. (1989) "A chemical kinetic model of vitrinite maturation and reflectance", Geochimica et Cosmochimica Acta, Vol. 53, pp. 2649-2657; and Sweeney, J. J., et al. (1990) "Evaluation of a Simple Model of Vitrinite Reflectance Based on Chemical Kinetics", AAPG Bulletin 74, pp. 1559-1570, which are incorporated herein by reference.

The quantitative simulation process 100 also executes a MCIF simulator 120 that uses ab initio estimates of carbon kinetic isotope effects to calculate the $^{13}C$ to $^{12}C$ ratio for each fraction of hydrocarbon over time. The quantitative simulation process 100 applies estimated constraints 118 on the timing of trap formation and rock volume of the hydrocarbon reservoir, which may be known or derived from the inputs 108, to analyze 122, such as create predictions. Examples of constraints 118 include, but are not limited to, fluid contacts (e.g., derived from seismic interpretations, structure maps, downhole logs, pressure data, fluid tests, and combinations thereof), reservoir geometry (e.g., derived from seismic interpretations, structure maps, downhole logs, numerical simulations, and combinations thereof), structural restorations (based on e.g., balanced cross-sections, seismic growth strata mapping, regional stratigraphic concepts, and combinations thereof), and the like, and any combination thereof.

The ab initio estimates of carbon kinetic isotope effects are applied to the individual reactions in the cascading cracking scheme with other inputs such as the temperature history of the hydrocarbon reservoir and/or source rock. More specifically, each isotopically-selective chemical reaction K is parameterized in two steps shown below.

The first step (1a) involves a precursor (A) reacting to form an intermediate (AB). In the second step (1b) of reaction K, the intermediate (AB) yields one or more products ($B_j$), where j=1, 2, ..., $n_{lumps}$, where $n_{lumps}$ is the number of products of reaction K. Written more explicitly, each chemical equation K is in the following form.

where quantities $a_k$ and $b_{jk}$ are stoichiometric (molar) coefficients.

The precursor (A) may be, for example, kerogen, coke, or a hydrocarbon per the cascading cracking scheme. The products ($B_j$) are hydrocarbons and optionally coke and/or inert char per the cascading cracking scheme.

Figure 2C:
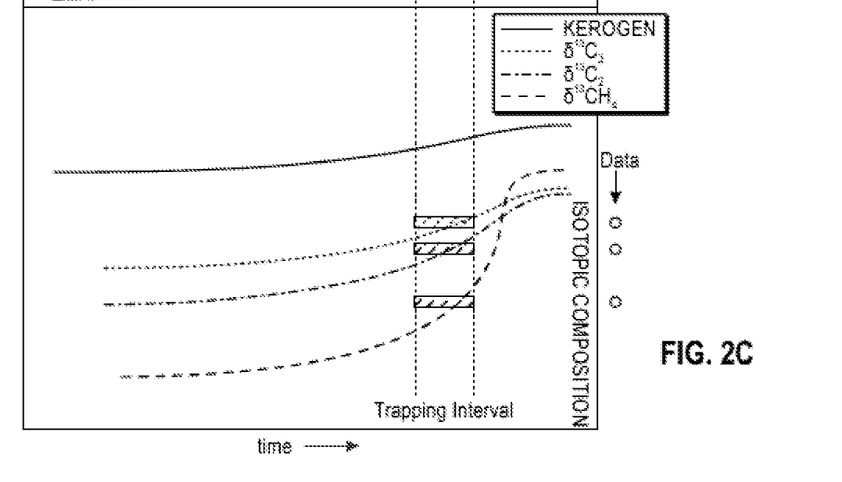
FIG. 2C illustrates a $^{13}C/^{12}C$ ratio (or abundance of $^{13}C$) vs. time plot for each of the hydrocarbon fractions, along with present-day sample data and timing of trap emplacement.

The compositional yields simulator 116 calculates values for $(^{12}C)_{Bj}$ during each time step for reaction K by: (i) determining how much of the remaining precursor in each of $n_{bins}$ $E_a$ bins (I) shall be cracked in said timestep, then (ii) reallocating the total mass of the $^{12}C$ intermediate $^{12}AB$ amongst the possible products $^{12}B_j$ according to a predefined table constructed, for example, from the estimated kinetic parameters 104. Additionally, in each timestep the MCIF simulator 120 reads the calculated masses of $^{12}C$ intermediates $^{12}AB$ and products $^{12}B_j$ and applies a temperature-dependent isotopic fractionation factor $(^{13}\alpha_{AB \to B}^{kin})$ to determine the $^{13}C/^{12}C$ ratio (or abundance of $^{13}C$) for each of the hydrocarbon fractions over time (FIG. 2C). The applicable corresponding set of reactions for the $^{13}C$-substituted variants of each reaction can be written as the following.

The kinetic carbon isotopic fractionation for each precursor-to-intermediate step (1a) is calculated as:

$$^{13}\alpha_k^{A \to AB} = \frac{^{13}\alpha_1 - 1}{\gamma_{A_k}} + 1, \text{ where } ^{13}\alpha_1 = func(T) \quad (2)$$

where $$^{13}\alpha_{A \to AB}^{kin} = \frac{(^{13}C/^{12}C)_J^{instantaneous}}{(^{13}C/^{12}C)_A} \text{ and } ^{13}\alpha_1^{kin} = \frac{(^{13}C/^{12}C)_{C1}^{instantaneous}}{(^{13}C/^{12}C)_{Ker1}}$$

and where the isotopic fractionation for $C_1$ is $^{13}\alpha_1^{kin}$.

This value may be derived from theoretical calculations such as those described in: Xiao, Y., 2001. Modeling the kinetics and mechanisms of petroleum and natural gas generation: A first principles approach. Reviews in Mineralogy and Geochemistry 42, pp. 383-436, which is incorporated herein by reference, and/or from experimental data from laboratory heating experiments of sedimentary organic matter such as those described in: Chung, H. M., et al. (1979) "Use of stable carbon isotope compositions of pyrolytically-derived methane as maturity indices for carbonaceous materials", Geochimica et Cosmochimica Acta, Vol. 43, pp. 1979-1988, which is incorporated herein by reference.

The kinetic carbon isotopic fractionation for each intermediate-to-product step (1b) is calculated as:

$$^{13}\alpha_k^{A \to AB} = \frac{^{13}\alpha_1 - 1}{\gamma_{B_j}} + 1$$

where: $^{13}\alpha_{A \to AB}^{kin} = \frac{(^{13}C/^{12}C)_B^{instantaneous}}{(^{13}C/^{12}C)_{AB}}$ and $$(^{13}C)_{B_j}^{unbal} = (^{12}C)_{B_j} \cdot (^{13}C/^{12}C)_{AB} \cdot ^{13}\alpha_{AB \to B}^{kin}.$$

The quantitative simulation process 100 compares 122 (a) the estimated maturity parameters from the maturity kinetic simulator 114, the yield versus time plot for each hydrocarbon fraction or combinations of hydrocarbon fractions from the compositional yields simulator 116, and the $^{13}C/^{12}C$ ratio (or abundance of $^{13}C$) for each of the hydrocarbon fractions over time to (b) the geochemical data, geophysical data, and/or geological data (inputs 108). Generally, the basin model 110 produces several possible geological scenarios to describe the hydrocarbon reservoir. The comparison 122 allows for (a) removing unlikely geological scenarios from the basin model 110 and (b) refining parameters within the basin model 110 and the constraints 118 for the MCIF simulator 120.

The quantitative simulation process 100 iteratively cycles (via an algorithm such as that shown in FIG. 4) through these analyses and estimates to produce likely prediction 122 that can be used as the basis for hydrocarbon management operations 124 in the hydrocarbon reservoir (e.g., exploring and producing hydrocarbons).

Specifically, the MCIF simulator algorithm solves a system of time-dependent ordinary differential equations (ODE's) for the amounts of carbon isotopes remaining in the source rock $(^{12}C)_{I,J}^{src}$ and $(^{13}C)_{I,J}^{src}$, the amounts of carbon isotopes expelled from the source rock $(^{12}C)_J^{src}$ and $(^{13}C)_J^{src}$. Said system of ODE's is represented by the following four equations:

$$\frac{d(^{12}C)_{I,J}^{src}}{dt} = -\frac{d(^{12}C)_{I,J}^{expelled}}{dt} - \sum_K {}^{12}k_{I,J,K}^{cracked} \cdot (^{12}C)_{I,J}^{src} + \sum_K {}^{12}k_{I,J}^{added} \cdot (^{12}C)_{I,J}^{src}$$

$$\frac{d(^{13}C)_J^{src}}{dt} = -\frac{d(^{12}C)_J^{expelled}}{dt} - \sum_K {}^{13}keff_{J,K}|_{j=k} \cdot (^{13}C)_J^{src} + \sum_K \frac{z_{jk}s_j}{\sum_J z_{jk}s_j} \cdot s_j$$

$$\frac{d(^{12}C)_J^{out}}{dt} = \sum_I \frac{d(^{12}C)_{J,J}^{expelled}}{dt}$$

$$\frac{d(^{13}C)_J^{out}}{dt} = \frac{d(^{13}C)_J^{expelled}}{dt}$$

where:

$$z_{jk} = (b_{jk}\gamma_{B_j}) \cdot {}^{13}\alpha_j^{AB \to B}$$

$$s_j = \sum_I {}^{13}keff_{J,K}|_{k=j} \cdot (^{13}C)_j^{src}$$

Figure 4:
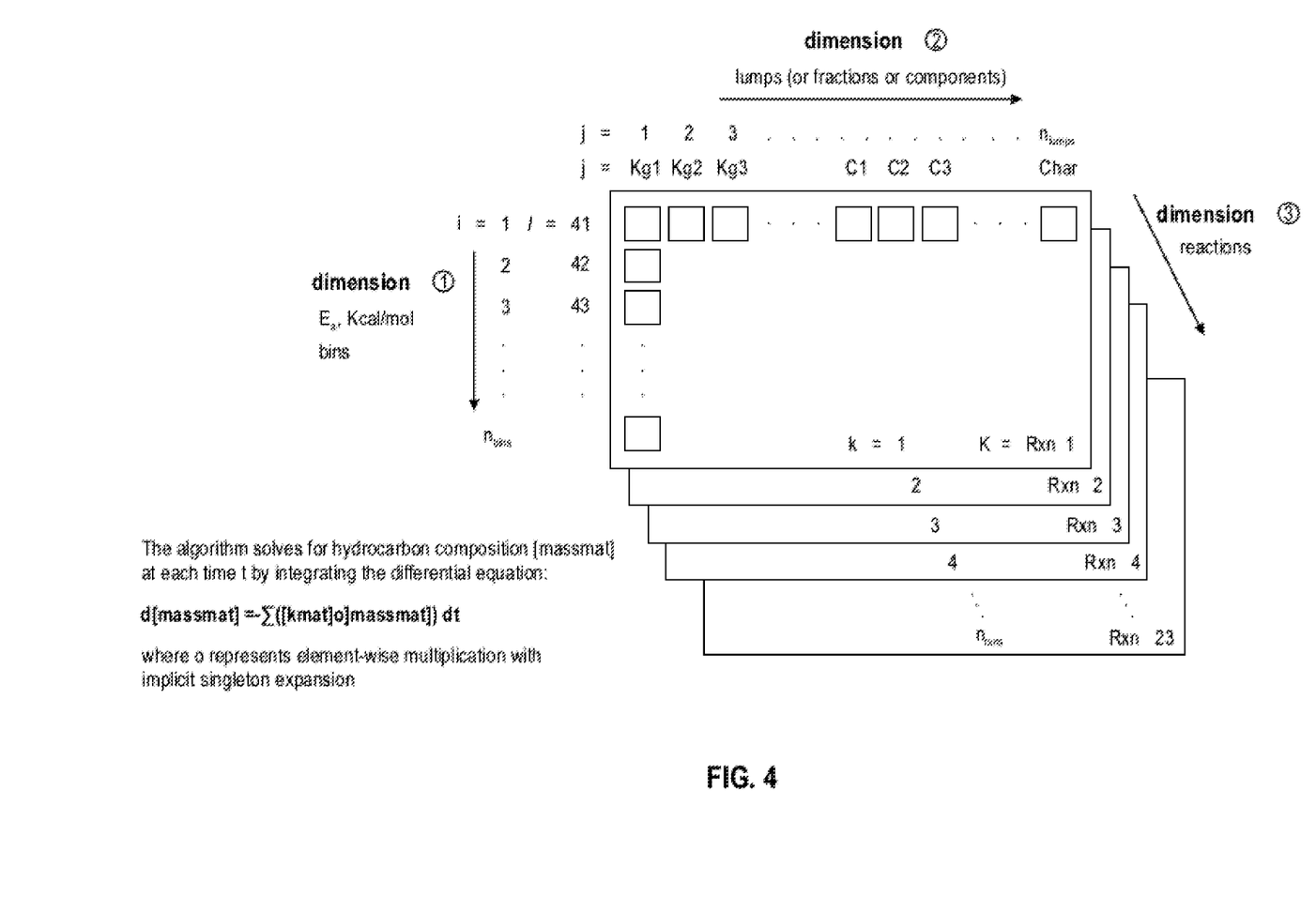
FIG. 4 is a diagrammatic representation of the core intermediate speciation matrix.

FIG. 4 is a diagrammatic representation of the core intermediate speciation matrix ([kmat], written in formulae as matrix k). Values of k are computed in each time step taken by the MCIF simulator in the following way:

$$^{12}k_{I,J,K}^{cracked} = \alpha_k \cdot A_j \cdot \exp(-I/RT)$$

$$^{12}k_{I,J,K} = b_{jk} \cdot A_j \cdot \exp(-I/RT)$$

$$^{13}keff_{J,K} = {}^{12}keff_{J,K} \cdot {}^{13}\alpha_k^{A \to AB}$$

where $^{12}keff$, the effective kinetic coefficient matrix, contains weighted means of the reaction rates for each set of $^{12}C$ first-order parallel reactions at discrete activation energies I:

$$^{12}keff_{J,K} = \frac{\sum_I ({}^{12}k_{I,J,K}^{cracked} \cdot (^{12}C)_{I,J}^{src})}{\sum_I (^{12}C)_{I,J}^{src}}$$

and where $I=(E_a)_i$ and $a_k=1$ for all reactions K, and $A_J$ is an array of frequency factors for the parallel unimolecular cracking reactions K of each lump J following the approach described in Hantschel, T., et al. (2009) "Petroleum Generation", Fundamentals of Basin and Petroleum Systems Modeling, Springer Berlin Heidelberg, pp. 151-198, which is incorporated herein by reference.

The increment in the amount of expelled hydrocarbon fractions $(^{12}C)_{I,J}^{expelled}$ and similarly, $(^{13}C)_{J}^{expelled})$ is determined at each time step via the method of Pepper, A. S. et al. (1995) "Simple kinetic models of petroleum formation. Part III: Modelling an open system", Marine and Petroleum Geology, Vol. 12, pp. 417-452, which is incorporated herein by reference.

Strictly, the temperature T and all spatially-varying source-rock parameters (such as TOC or HI) are functions of t, x, y, and z, the latter three variables representing 3-dimensional Cartesian space, and hence the numerical problem addressed in this disclosure requires solving a system of partial differential equations (PDE's). For a 1-dimensional basin model and a single source horizon, the equations reduce to the ODE's above.

The above system of differential equations can be discretized and solved by a numerical solution method. For example, the system of differential equations was solved in MATLAB™ using the Runge-Kutta solver ode15s. Solver parameters included a maximum time step of 1 Myr, a relative error tolerance of 0.0001%, and an absolute error tolerance of $(1\times10^{-6})\times m_{start}$, where $m_{start}$ is the initial mass of carbon in the simulation (the value of which may be calculated from data 108 or extracted from kinetic model 106). Mass was considered to be conserved if the ending total amounts of $^{12}C$ and $^{13}C$ agree to within 0.00100% of their starting values.

The MCIF simulation algorithm 120 is a unique addition for estimating the isotopic composition of the hydrocarbon fractions J, and the analysis 122, such as the predictions produced by the quantitative simulation process 100 allow for evaluating hydrocarbon reservoirs of any size. For example, the predictions provide information such as if a source rock exists, if a hydrocarbon trap was in place before the source rock began generating hydrocarbons, if and for how long the source rock was/is still generating hydrocarbons, and if a conduit exists between the source rock and the hydrocarbon reservoir.

Additionally, the quantitative simulation process 100 may analyze data in FIGS. 2B and 2C to determine when hydrocarbon production may have the most yield. As illustrated in FIG. 2C, the dots on the right of the plot may be geochemical data for the abundance of $^{13}C$ in $C_1$, $C_2$, and $C_3$ hydrocarbons. Because the time is a time evolution of the hydrocarbon reservoir and not set to a specific time, the geochemical data for the abundance of $^{13}C$ in $C_1$, $C_2$, and $C_3$ hydrocarbons can be translated to the plot (blocks in the plot) to approximate where current time is on the time axis. Then, moving up to FIG. 2B, the estimated yields can be narrowed. In the illustrated example, the gas ($C_1$-$C_4$ portion) estimated yield is increasing and the oil ($C_{5+}$) estimated yield is peaked or declining. Therefore, depending on the hydrocarbon class desired for a production operation, hydrocarbon management operations 124 can make a decision to explore for or produce the hydrocarbon reservoir now or in the future.

Additionally, the quantitative simulation process 100 advantageously has the ability to simulate chemical and isotopic hydrocarbon compositions accumulated over different trapping intervals. In contrast, previous models (e.g., Chung, H. M., et al. (1988) "Origin of gaseous hydrocarbons in subsurface environments: theoretical considerations of carbon isotope distribution", Chemical Geology, Vol. 71, pp. 97-104; Rooney, M. A., et al., (1995) "Modeling thermogenic gas generation using carbon isotope ratios of natural gas hydrocarbons", Chemical Geology, Vol. 126, pp. 219-232; Tang, Y., et al. (2000) "Mathematical modeling of stable carbon isotope ratios in natural gases", Geochimica et Cosmochimica Acta, Vol. 64, No. 15, pp. 2673-2687), are able to model only the isotopic compositions of gas at a particular instant and/or total generated gas. The quantitative simulation process 100 described herein can be used to predict the "semi-cumulative" composition of hydrocarbons trapped in real reservoirs under varying assumptions about trap timing. This is achieved by accepting as input a user-defined trapping interval (based on subsurface or outcrop data, which may be portions of inputs 108) for expelled hydrocarbons as shown in FIG. 2. Hydrocarbon volumes expelled from source rock are calculated following a standard retention-adsorption scheme. Then, if a potential trap formed at time $t_i$ and received charge until time $t_f$ (=0 Ma, or earlier if, for example, a migration shadow developed), the quantitative simulation process 100 determines the quantity and isotope ratio of each compound accumulated in the trap as follows (where $^{1x}C$ may be $^{13}C$ or $^{12}C$):

$$(^{1x}C)_{B_j}^{trapped} = \Sigma_{t_i}^{t_f} \Sigma_j (^{1x}C)_{B_j}^{expelled\ @\ time\ t}$$

Further, the quantitative simulation process 100 described herein may also be useful in evaluating the probability of achieving economic trapped volumes or column heights of hydrocarbon when timing of structure emplacement or seal formation relative to maturation through the oil- or gas-window poses a key geologic risk. Inferences on trap timing derived from predictions can be compared to geological constraints on trap timing (e.g., growth in pre- and post-reservoir interval stratigraphy) to determine extents of source kitchens and drainage areas at the critical moment for the hydrocarbon system.

Various aspects of the systems and methods described herein utilize computer systems. Such systems and methods can include a non-transitory computer readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and prior art-recognized equivalents and successor media, in which the software implementations embodying the present techniques are stored.

The methods described herein can, and in many embodiments must, be performed using computing devices or processor-based devices that include a processor; a memory coupled to the processor; and instructions provided to the memory, wherein the instructions are executable by the processor to perform the methods described herein (such computing or processor-based devices may be referred to generally by the shorthand "computer"). For example, any one or more of the following may be carried out using a computer: measuring a chemical and isotopic composition of a hydrocarbon sample from a hydrocarbon reservoir; measuring geochemical data, geophysical data, and/or geological data for the hydrocarbon reservoir; deriving temperature versus time relationships from a basin model for the hydrocarbon reservoir based on the geochemical data, geophysical data, and/or geological data; generating estimated source-rock maturity parameters based on the temperature versus time relationship; generating an estimated compositional yield for hydrocarbon fractions from the hydrocarbon reservoir based on the temperature versus time relationships and the chemical composition of the hydrocarbon sample; generating, using the MCIF simulator, an estimated isotopic composition of the hydrocarbon fractions based on the estimated compositional yield and the isotopic composition of the hydrocarbon sample; and performing a hydrocarbon management operation in the hydrocarbon reservoir based on the estimated source-rock maturity parameters, the estimated compositional yield, and the estimated isotopic composition.

Furthermore, the instructions of such computing devices or processor-based devices can be a portion of code on a non-transitory computer-readable medium. Any suitable processor-based device may be utilized for implementing all or a portion of embodiments of the present techniques, including without limitation personal computers, networks of personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

The methods and systems described herein may all be deployed in managing hydrocarbons in the hydrocarbon reservoir. As used herein, "managing hydrocarbons" or "hydrocarbon management" includes any one or more of the following: hydrocarbon extraction; hydrocarbon production, (e.g., drilling a well and prospecting for, and/or producing, hydrocarbons using the well; and/or, causing a well to be drilled, e.g., to prospect for hydrocarbons); hydrocarbon exploration; identifying potential hydrocarbon systems such as those including hydrocarbon-bearing formations; determining candidate-sampling locations within a hydrocarbon system; evaluating a hydrocarbon system; characterizing a hydrocarbon system such as a hydrocarbon-bearing formation; identifying well locations; determining well injection rates; determining well extraction rates; identifying reservoir connectivity; acquiring, disposing of, and/or abandoning hydrocarbon resources; reviewing prior hydrocarbon management decisions; and any other hydrocarbon-related acts or activities, such activities typically taking place with respect to a hydrocarbon system and/or subsurface formation. In particular embodiments, managing hydrocarbons may include one or more of identifying a zone of the hydrocarbon reservoir for completion, and carrying out one or more completion operations on or in the identified zone; identifying a portion of the hydrocarbon reservoir from where to obtain a core sample for further analysis, and obtaining one or more core samples from the identified portion; carrying out a simulation or completion operation on the hydrocarbon reservoir; and/or identifying a horizontal well landing location within the hydrocarbon reservoir and causing a horizontal well to be drilled to the identified landing location. The aforementioned broadly include not only the acts themselves (e.g., extraction, production, drilling a well, etc.), but also or instead the direction and/or causation of such acts (e.g., causing hydrocarbons to be extracted, causing hydrocarbons to be produced, causing a well to be drilled, causing the prospecting of hydrocarbons, etc.).

Example Embodiments

A first nonlimiting example embodiment of the present disclosure is a quantitative simulation process comprising: measuring a chemical and isotopic composition of a hydrocarbon sample from a hydrocarbon reservoir; measuring geochemical data, geophysical data, and/or geological data for the hydrocarbon reservoir and/or source rock; deriving temperature versus time relationships from a basin model for the hydrocarbon reservoir and/or source rock based on the geochemical data, geophysical data, and/or geological data; generating estimated source-rock maturity parameters based on the temperature versus time relationships; generating an estimated compositional yield for hydrocarbon fractions from the hydrocarbon reservoir based on the temperature versus time relationships and the chemical composition of the hydrocarbon sample; generating, using a mass-conserving isotopic fraction (MCIF) simulator that uses ab initio calculations, an estimated isotopic composition of the hydrocarbon fractions based on the estimated compositional yield and the isotopic composition of the hydrocarbon sample; and performing a hydrocarbon management operation in the hydrocarbon reservoir based on the estimated source-rock maturity parameters, the estimated compositional yield, and the estimated isotopic composition. The first nonlimiting example embodiment may include one or more of: Element 1: wherein the basin model is a 1-dimensional basin model, 2-dimensional basin model, or 3-dimensional basin model; Element 2: wherein constraints of the quantitative simulation process are selected from the group consisting of: a timing of trap formation and/or a rock volume of the hydrocarbon reservoir; Element 3: Element 2 and wherein the constraints of the quantitative simulation process are based on a factor selected from the group consisting of: fluid contacts, reservoir geometry, structural restorations, and any combination thereof; Element 4: the quantitative simulation process further comprising: comparing the estimated source-rock maturity parameters, estimated compositional yield, and estimated isotopic composition to the geochemical data, geophysical data, and/or geological data; adjusting the basin model and/or the MCIF simulator calculations or inputs thereof; and iteratively performing the steps of the deriving temperature versus time relationships from the basin model, the generating estimated source-rock maturity parameters, the generating an estimated compositional yield, the generating the estimated isotopic composition; the comparing, and the adjusting before performing the hydrocarbon management operation; and Element 5: wherein the hydrocarbon management operation is selected from the group consisting of: hydrocarbon extraction, hydrocarbon production, hydrocarbon exploration, identifying potential hydrocarbon systems, determining candidate-sampling locations within a hydrocarbon system, evaluating a hydrocarbon system, characterizing a hydrocarbon system, identifying a well location, determining a well injection rate, determining a well extraction rate, identifying reservoir connectivity, acquiring hydrocarbon resources, disposing of hydrocarbon resources, abandoning hydrocarbon resources, reviewing prior hydrocarbon management decisions, and any combination thereof. Examples of combinations include, but are not limited to, Element 1 in combination with one or more of Elements 2-5; Element 2 (optionally in combination with Element 3) in combination with Element 4 and/or Element 5; and Elements 4-5 in combination.

A second nonlimiting example embodiment is a system comprising: a processor; a non-transitory, computer-readable medium; a non-transitory, computer-readable medium comprising instructions configured to perform the method of the first nonlimiting example embodiment (optionally in combination with one or more of Elements 1-5). Said system may be a combination of instruments and/or computers.

A third nonlimiting example embodiment is a computing system comprising: a processor; a non-transitory, computer-readable medium comprising a quantitative simulation process that derives an estimated source-rock maturity parameters, an estimated compositional yield, and an estimated isotopic composition for a hydrocarbon reservoir; a non-transitory, computer-readable medium comprising instructions configured to: accept inputs that include geochemical data, geophysical data, and/or geological data for the hydrocarbon reservoir and a chemical and isotopic composition of a hydrocarbon sample from the hydrocarbon reservoir; and run the quantitative simulation process that comprises: a basin model for the hydrocarbon reservoir that produces temperature versus time relationships based on the geochemical data, geophysical data, and/or geological data; a maturity kinetic simulator that produces estimated source-rock maturity parameters based on the temperature versus time relationships; a compositional simulator that produces an estimated compositional yield for hydrocarbon fractions from the hydrocarbon reservoir based on the temperature versus time relationships and the chemical composition of the hydrocarbon sample; a mass-conserving isotopic fraction simulator, which uses ab initio calculations, that produces an estimated isotopic composition of the hydrocarbon fractions based on the estimated compositional yield and the isotopic composition of the hydrocarbon sample; and output the estimated source-rock maturity parameters, the estimated compositional yield, and the estimated isotopic composition. The third nonlimiting example embodiment may further include one or more of: Element 6: wherein the basin model is a 1-dimensional basin model, 2-dimensional basin model, or 3-dimensional basin model; Element 7: wherein constraints of the quantitative simulation process are selected from the group consisting of: a timing of trap formation and/or a rock volume of the hydrocarbon reservoir; Element 8: Element 7 and wherein the constraints of the quantitative simulation process are based on a factor selected from the group consisting of: fluid contacts, reservoir geometry, structural restorations, and any combination thereof; Element 9: wherein the instructions are further configured to: compare the estimated source-rock maturity parameters, estimated compositional yield, and estimated isotopic composition to the geochemical data, geophysical data, and/or geological data; adjusting the basin model and/or the MCIF simulator calculations or inputs thereof; and iteratively perform the steps of the deriving temperature versus time relationships from the basin model, the generating estimated source-rock maturity parameters, the generating an estimated compositional yield, the generating the estimated isotopic composition; the comparing, and the adjusting before performing the hydrocarbon management operation; Element 10: wherein the instructions are further configured to: simulate a hydrocarbon management operation based on the estimated source-rock maturity parameters, the estimated compositional yield, and the estimated isotopic composition; Element 11: Element 10 and wherein the hydrocarbon management operation is selected from the group consisting of: hydrocarbon extraction, hydrocarbon production, hydrocarbon exploration, identifying potential hydrocarbon systems, determining candidate-sampling locations within a hydrocarbon system, evaluating a hydrocarbon system, characterizing a hydrocarbon system, identifying a well location, determining a well injection rate, determining a well extraction rate, identifying reservoir connectivity, acquiring hydrocarbon resources, disposing of hydrocarbon resources, abandoning hydrocarbon resources, reviewing prior hydrocarbon management decisions, and any combination thereof; Element 12: wherein the instructions are further configured to: cause one or more components of a system to function for a hydrocarbon management operation based on the estimated source-rock maturity parameters, the estimated compositional yield, and the estimated isotopic composition; and Element 13: Element 12 and wherein the hydrocarbon management operation is selected from the group consisting of: hydrocarbon extraction, hydrocarbon production, hydrocarbon exploration, identifying potential hydrocarbon systems, determining candidate-sampling locations within a hydrocarbon system, evaluating a hydrocarbon system, characterizing a hydrocarbon system, identifying a well location, determining a well injection rate, determining a well extraction rate, identifying reservoir connectivity, acquiring hydrocarbon resources, disposing of hydrocarbon resources, abandoning hydrocarbon resources, reviewing prior hydrocarbon management decisions, and any combination thereof. Examples of combinations include, but are not limited to, Element 6 in combination with one or more of Elements 7-9; Element 7 in combination with Element 8 optionally in combination with Element 9; Element 10 (and optionally Element 11) in combination with one or more of Elements 6-9; and Element 12 (and optionally Element 13) in combination with one or more of Elements 6-9.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Figure 5:
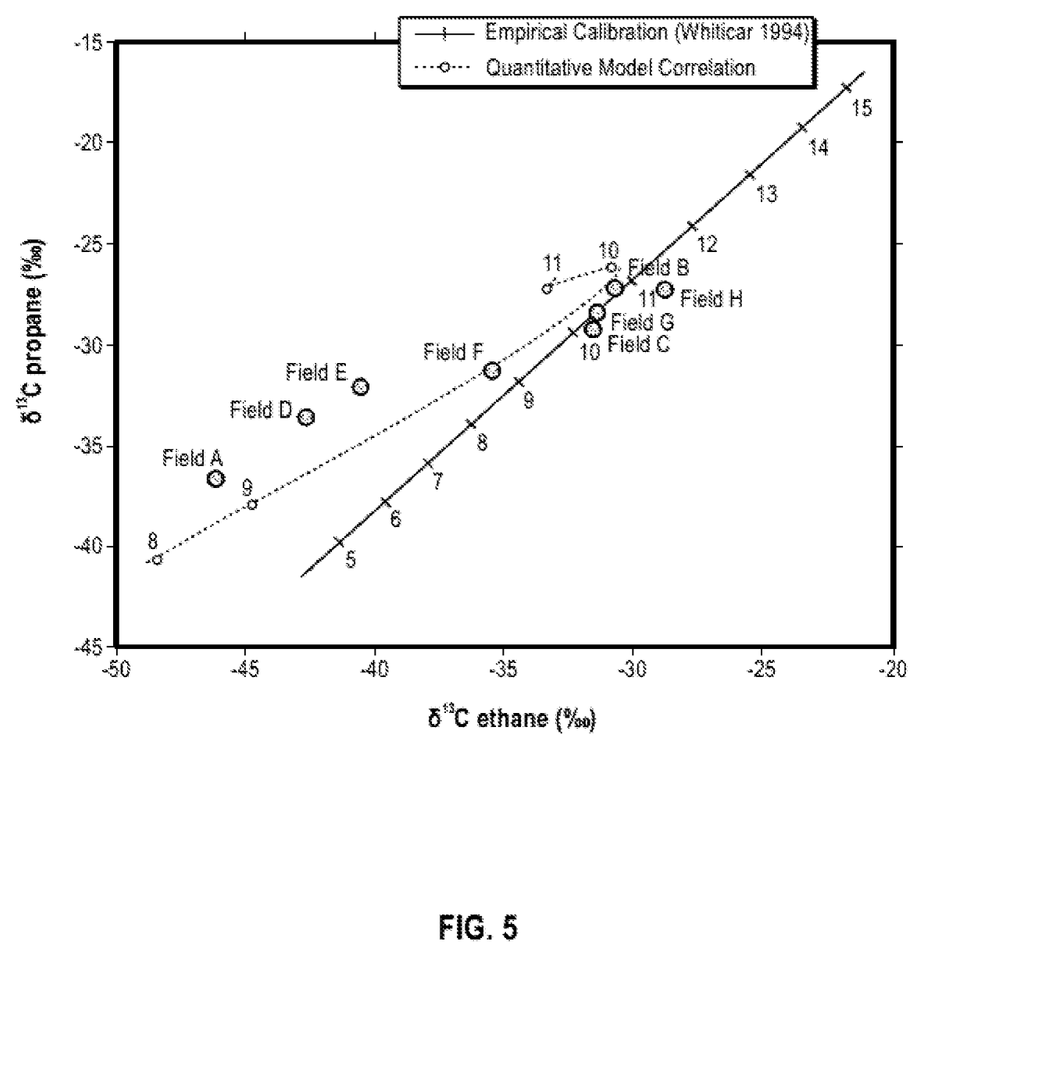
FIG. 5 is a plot of $\delta^{13}C_2$ where $\delta^{13}C_3$, where $\delta^{13}C_n=[(^{13}C_n/^{12}C_n)_{sample}/(^{13}C_n/^{12}C_{reference}]-1$, along with trajectories representing predicted values of $\delta^{13}C_2$ and $\delta^{13}C_3$ over a range of relative thermal maturities represented by the numerical values 5 through 15, with increasing maturity represented by increasing values.

Several numerical simulations of test geologic scenarios were simulated using a quantitative simulation process described herein. FIGS. 4 and 5 show the result of a calculation performed using default assumptions for a generic sedimentary basin containing a Type II source rock as compared to public and proprietary data from hydrocarbon reservoirs of the U.S. Gulf of Mexico, offshore California, and North Sea.

FIG. 5 is a plot of $\delta^{13}C_2$ versus $\delta^{13}C_3$, where $\delta^{13}C_n = [(^{13}C_n/^{12}C_n)_{sample}/(^{13}C_n/^{12}C_n)_{reference}]-1$. FIG. 5 illustrates (1—large dots) the measured data of $\delta^{13}C_2$ and $\delta^{13}C_3$ isotope ratio values for the hydrocarbon reservoirs in this data set, (2—solid line) the widely-used Whiticar correlation line (Whiticar, M. J., 1994, Correlation of natural gases with their sources. Chap. 16 in The Petroleum System—From Source to Trap: AAPG Memoir 60 (Magoon and Dow, eds.), pp. 261-283) with a calibration of $\delta^{13}C_2:\delta^{13}C_3$ ratio to maturity (number by tick mark) of the source rock, and (3—dashed line) the quantitative simulation process correlation of $\delta^{13}C_2:\delta^{13}C_3$ ratio to maturity (number by small dot) of the source rock. The quantitative simulation process more closely approximates the measured data as compared to the Whiticar line.

Figure 6:
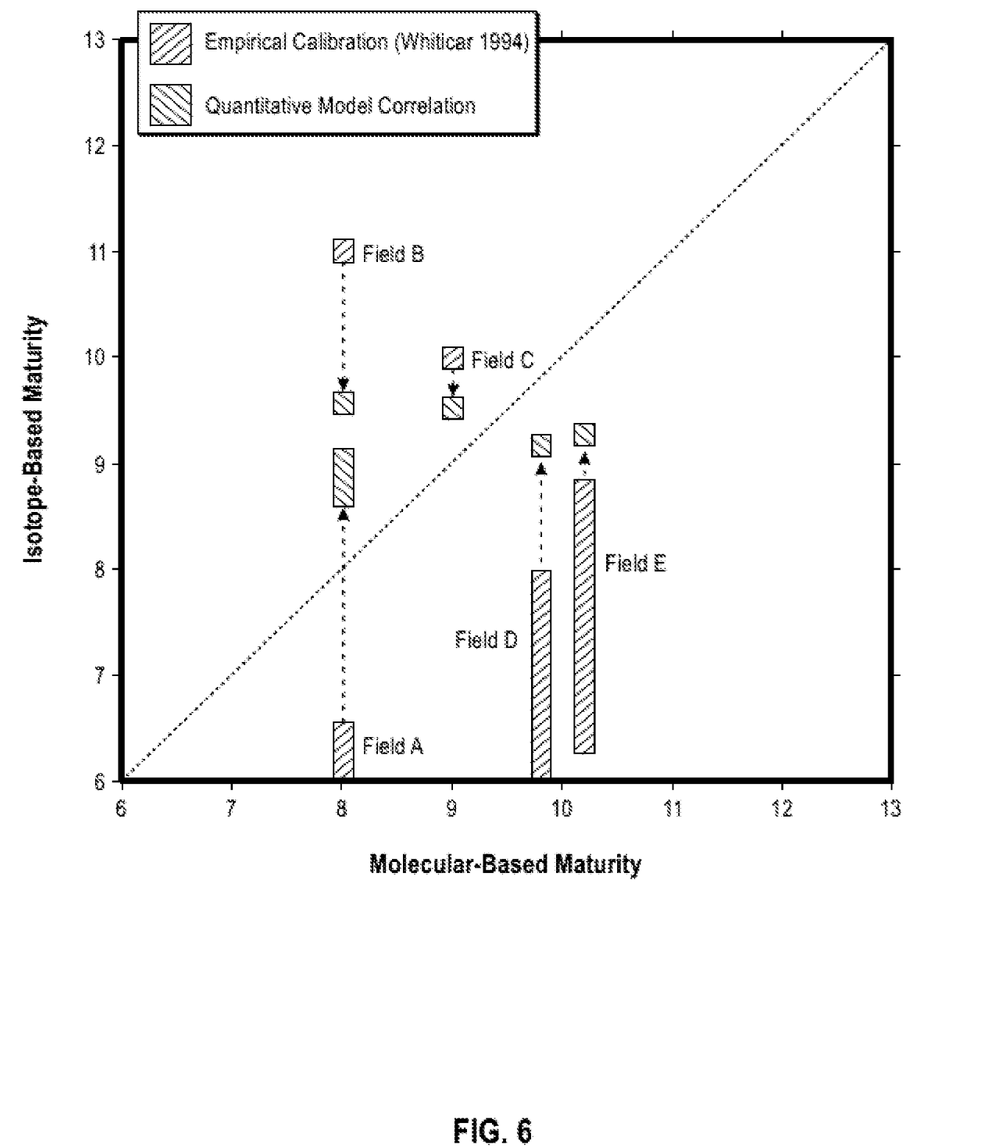
FIG. 6 is a plot of the estimated maturity of the source rock versus the measured maturity for source rocks in the dataset presented in FIG. 5.

FIG. 6 is a plot of the estimated maturity of the source rock versus the measured maturity for source rocks having a 7-10 maturity in the dataset presented in FIG. 5. The estimates from the quantitative simulation process described herein more closely match the measured values (being closer to the 1:1:line) as compared to the Whiticar model. The quantitative simulation process therefore allows gas data to be integrated with standard geochemical interpretations. The quantitative simulation process described herein could be applied during exploration to evaluate maturity of gas shows and discoveries, particularly where gas is predominant and little/no biomarker information is available. Potential assets and acreage to which the quantitative simulation process described herein may be applied in the future include gas-rich deep water provinces, geologic plays with terrestrially-sourced organic matter, and high-maturity unconventional hydrocarbon reservoirs.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A process comprising:
   measuring a chemical and isotopic composition of a hydrocarbon sample from a hydrocarbon reservoir;
   measuring geochemical data, geophysical data, and/or geological data for the hydrocarbon reservoir and/or a source rock;
   deriving temperature versus time relationships from a basin model for the hydrocarbon reservoir and/or source rock based on the geochemical data, geophysical data, and/or geological data;
   generating estimated source-rock maturity parameters based on the temperature versus time relationships;
   generating an estimated compositional yield for hydrocarbon fractions from the hydrocarbon reservoir based on the temperature versus time relationships and the chemical composition of the hydrocarbon sample;
   generating, using a mass-conserving isotopic fraction (MCIF) simulator that uses ab initio calculations, an estimated isotopic composition of the hydrocarbon fractions based on the estimated compositional yield and the isotopic composition of the hydrocarbon sample; and
   performing a hydrocarbon management operation in the hydrocarbon reservoir based on the estimated source-rock maturity parameters, the estimated compositional yield, and the estimated isotopic composition.

2. The process of claim 1, wherein the basin model is a 1-dimensional basin model, 2-dimensional basin model, or 3-dimensional basin model.

3. The process of claim 1, wherein constraints of the quantitative simulation process are selected from the group consisting of: a timing of trap formation and/or a rock volume of the hydrocarbon reservoir.

4. The process of claim 3, wherein the constraints of the quantitative simulation process are based on a factor selected from the group consisting of: fluid contacts, reservoir geometry, structural restorations, and any combination thereof.

5. The process of claim 1, further comprising:
   comparing the estimated source-rock maturity parameters, estimated compositional yield, and estimated isotopic composition to the geochemical data, geophysical data, and/or geological data;

adjusting the basin model and/or the MCIF simulator calculations or inputs thereof; and iteratively performing the steps of the deriving temperature versus time relationships from the basin model, the generating estimated source-rock maturity parameters, the generating an estimated compositional yield, the generating the estimated isotopic composition; the comparing, and the adjusting before performing the hydrocarbon management operation.

6. The process of claim 1, wherein the hydrocarbon management operation is selected from the group consisting of: hydrocarbon extraction, hydrocarbon production, hydrocarbon exploration, identifying potential hydrocarbon systems, determining candidate-sampling locations within a hydrocarbon system, evaluating a hydrocarbon system, characterizing a hydrocarbon system, identifying a well location, determining a well injection rate, determining a well extraction rate, identifying reservoir connectivity, acquiring hydrocarbon resources, disposing of hydrocarbon resources, abandoning hydrocarbon resources, reviewing prior hydrocarbon management decisions, and any combination thereof.

7. A computing system comprising:
a processor;
a non-transitory, computer-readable medium comprising a quantitative simulation process that derives estimated source-rock maturity parameters, an estimated compositional yield, and an estimated isotopic composition for a hydrocarbon reservoir;
the non-transitory, computer-readable medium comprising instructions configured to:
  accept inputs that include geochemical data, geophysical data, and/or geological data for the hydrocarbon reservoir and a chemical and isotopic composition of a hydrocarbon sample from the hydrocarbon reservoir; and
  run the quantitative simulation process that comprises:
    a basin model for the hydrocarbon reservoir that produces temperature versus time relationships based on the geochemical data, geophysical data, and/or geological data;
    a maturity kinetic simulator that produces estimated source-rock maturity parameters based on the temperature versus time relationships;
    a compositional simulator that produces an estimated compositional yield for hydrocarbon fractions from the hydrocarbon reservoir based on the temperature versus time relationships and the chemical composition of the hydrocarbon sample; and
    a mass-conserving isotopic fraction (MCIF) simulator, which uses ab initio calculations, that produces an estimated isotopic composition of the hydrocarbon fractions based on the estimated compositional yield and the isotopic composition of the hydrocarbon sample; and
  output the estimated source-rock maturity parameters, the estimated compositional yield, and the estimated isotopic composition.

8. The computing system of claim 7, wherein the basin model is a 1-dimensional basin model, 2-dimensional basin model, or 3-dimensional basin model.

9. The computing system of claim 7, wherein constraints of the quantitative simulation process are selected from the group consisting of: a timing of trap formation and/or a rock volume of the hydrocarbon reservoir.

10. The computing system of claim 9, wherein the constraints of the quantitative simulation process are based on a factor selected from the group consisting of: fluid contacts, reservoir geometry, structural restorations, and any combination thereof.

11. The computing system of claim 7, wherein the instructions are further configured to:
compare the estimated source-rock maturity parameters, estimated compositional yield, and estimated isotopic composition to the geochemical data, geophysical data, and/or geological data;
adjusting the basin model and/or the MCIF simulator calculations or inputs thereof; and
iteratively perform the steps of the deriving temperature versus time relationships from the basin model, the generating estimated source-rock maturity parameters, the generating an estimated compositional yield, the generating the estimated isotopic composition; the comparing, and the adjusting before performing the hydrocarbon management operation.

12. The computing system of claim 7, wherein the instructions are further configured to:
simulate a hydrocarbon management operation based on the estimated source-rock maturity parameters, the estimated compositional yield, and the estimated isotopic composition.

13. The computing system of claim 12, wherein the hydrocarbon management operation is selected from the group consisting of: hydrocarbon extraction, hydrocarbon production, hydrocarbon exploration, identifying potential hydrocarbon systems, determining candidate-sampling locations within a hydrocarbon system, evaluating a hydrocarbon system, characterizing a hydrocarbon system, identifying a well location, determining a well injection rate, determining a well extraction rate, identifying reservoir connectivity, acquiring hydrocarbon resources, disposing of hydrocarbon resources, abandoning hydrocarbon resources, reviewing prior hydrocarbon management decisions, and any combination thereof.

14. The computing system of claim 7, wherein the instructions are further configured to:
cause one or more components of a system to function for a hydrocarbon management operation based on the estimated source-rock maturity parameters, the estimated compositional yield, and the estimated isotopic composition.

15. The computing system of claim 14, wherein the hydrocarbon management operation is selected from the group consisting of: hydrocarbon extraction, hydrocarbon production, hydrocarbon exploration, identifying potential hydrocarbon systems, determining candidate-sampling locations within a hydrocarbon system, evaluating a hydrocarbon system, characterizing a hydrocarbon system, identifying a well location, determining a well injection rate, determining a well extraction rate, identifying reservoir connectivity, acquiring hydrocarbon resources, disposing of hydrocarbon resources, abandoning hydrocarbon resources, reviewing prior hydrocarbon management decisions, and any combination thereof.

* * * * *